United States Patent [19]

Holtz et al.

[11] 3,931,236

[45] Jan. 6, 1976

[54] OXIDATION AND DEHYDROHALOGENATION OF HALOTETRAHYDROPYRANS

[75] Inventors: Hans D. Holtz; John E. Mahan, both of Bartlesville, Okla.

[73] Assignee: Phillips Petroleum Company, Bartlesville, Okla.

[22] Filed: Apr. 17, 1973

[21] Appl. No.: 351,980

[52] U.S. Cl. ............................................. 260/343.5
[51] Int. Cl.$^2$ ...................................... C07D 309/30
[58] Field of Search .................................. 260/343.5

[56] References Cited
UNITED STATES PATENTS
2,453,890  11/1948  Bremner et al. ................. 260/343.5
3,527,771  9/1970  Stapp ............................ 260/345.1

OTHER PUBLICATIONS
Wagner and Zook, Synthetic Organic Chemistry, New York, Wiley & Sons, 1953, pp. 35–38 relied on.

*Primary Examiner*—Donald G. Daus
*Assistant Examiner*—Anne Marie T. Tighe

[57] ABSTRACT

A halotetrahydropyran is oxidized and dehydrohalogenated employing oxygen and a free radical initiator.

4-Chlorotetrahydropyran is converted to 5,6-dihydro-1,2-pyrone using 2,2'-azobis(2-methylpropionitrile) under elevated oxygen pressure and at a temperature of the order of about 170°F.

3 Claims, No Drawings

OXIDATION AND DEHYDROHALOGENATION OF HALOTETRAHYDROPYRANS

This invention relates to the oxidation and dehydrohalogenation of a halotetrahydropyran. In one of its aspects, it relates to the production of a dihydropyrone, e.g., 5,6-dihydro-1,2-pyrone, employing an oxidation and dehydrohalogenation process.

In one of its concepts, the invention provides a process for the production of a dihydropyrone by oxidation and dehydrohalogenation of a halotetrahydropyran in the presence of oxygen or an oxygen-containing gaseous medium and a free radical initiator at ordinary, but preferably an elevated temperature, the partial pressure of oxygen being about 2-200 psig which is sufficient to accomplish the oxidation and dehydrohalogenation. It is to be noted that U.S. Pat. No. 3,527,771 describes and claims the thermal dehydrohalogenation of 4-halotetrahydropyrans such as 4-chlorotetrahydropyran in the temperature range of 400° to 600°C.

We have now discovered, quite unexpectedly, when attempting to produce a chlorolactone from 4-chlorotetrahydropyran by free radical oxidation that the major product of the oxidation is, in fact, the unsaturated lactone. Thus, we have discovered that oxidation and dehydrohalogenation occurs in the presence of oxygen or oxygen-containing gas and a free radical initiator to yield the unsaturated lactone or dihydropyrone and this at a relatively quite low, even in fact ordinary temperature.

It is an object of this invention to produce a dihydropyrone. It is another object of this invention to oxidize and dehydrohalogenate a halotetrahydropyran at a relatively low temperature. It is a further object of the invention to produce 5,6-dihydro-1,2-pyrone. Still another object of the invention is to oxidize and dehydrohalogenate a halotetrahydropyran at low or ordinary temperatures.

Other aspects, concepts, objects, and the several advantages of the invention are apparent from a study of this disclosure and the appended claims.

According to the present invention, there is provided a process for the oxidation and dehydrohalogenation of a halotetrahydropyran to form a dihydropyrone or unsaturated lactone which comprises contacting the halotetrahydropyran with oxygen or an oxygen-containing gas in the presence of a free radical initiator for a time sufficient to effect the desired conversion.

As noted, the reaction takes place at ordinary temperatures. However, an elevated temperature is now preferred as given herein.

Conditions including temperature, reaction time and partial pressure of oxygen, as well as the free radical initiator selected, can be varied considerably within the scope of the broad concept of the invention. One skilled in the art in possession of this disclosure having studied the same will understand that the reaction which can be achieved is a discovery upon which this application for patent is based. Given the conditions herein, depending upon the starting material or materials and product or products sought to be obtained, the conditions can be determined by routine testing.

Thus, in accordance with the present invention, halotetrahydropyran such as 4-chlorotetrahydropyran and 3-bromotetrahydropyran (A) are converted to 5,6-dihydro-1,2-pyrone (B) in the presence of oxygen and a free radical initiator such as 2,2'-azobis(2-methylpropionitrile) (AIBN) as shown below:

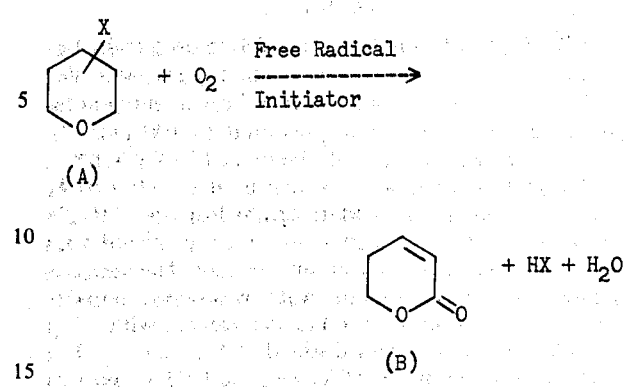

wherein X represents bromine, chlorine or iodine and the halogen is attaching the three or four position of the tetrahydropyran ring.

Free radical initiators which can be used include such as 2,2'-azobis(2-methylpropionitrile) (AIBN), di-tert-butyl peroxide, tert-butyl hydroperoxide, cumyl peroxide, benzoyl peroxide, cumene hydroperoxide, and the like.

In a now preferred embodiment, the feedstock (A) is 4-chlorotetrahydropyran and the free radical initiator is 2,2'-azobis(2-methylpropionitrile) (AIBN). Other suitable feedstocks include 4- and 3-bromotetrahydropyran, 4- and 3-iodotetrahydropyran and 3-chlorotetrahydropyran.

The following approximate parameters are suitable for the practice of the present invention:

| Parameter | Suitable | Preferred |
|---|---|---|
| Temperature, °C | 30–180 | 50–130 |
| Reaction Time (Hours) | 0.1–100 | 5–50 |
| Partial Pressure Oxygen (psig) | 2–200 | 50–100 |

Pure oxygen can be used; however, there can be used an inert diluent such as nitrogen, neon, helium, argon, krypton, and xenon.

Safety considerations dictate against the use of the upper end of the temperature range coupled with the upper limit of the oxygen partial pressure range. In general, lower temperatures will require longer reaction periods to attain a specified conversion at constant oxygen pressure. Reaction temperatures generally will be higher than the decomposition temperature of the initiator used. Such temperatures are well known in the art for the used initiators.

Halogenated aromatic compounds such as aryl chlorides and aryl fluorides are solvents useful in the present process. Suitable solvents or diluents include chlorobenzene, fluorobenzene, ortho-dichlorobenzene, 1,2,4-trichlorobenzene, 1,3,5-trichlorobenzene, meta-difluorobenzene, para-dichlorobenzene, 1-chloronaphthalene, 1-fluoronaphthalene, meta-dichlorobenzene, and the like, mixtures thereof.

The present process can be carried out in conventional pressure vessels which are made of materials resistant to the corrosive effects of the hydrohalic acid by-product. Presently a glass-lined Parr titanium autoclave is preferred although all glass pressure reactors are suitable.

The following is an example enabling one skilled in the art to perform the invention and to conduct routine experimentation rendered obvious by this disclosure.

EXAMPLE I

A 55.6 g (0.46 mole) sample of 4-chlorotetrahydropyran and 0.3 g 2,2'-azobis(2-methylpropionitrile) (AIBN) was placed in a glass-lined Parr titanium autoclave and the system was pressured to 100 psig $O_2$. After a reaction period of 46 hours at 170°F (76.6°C), the reaction mixture was distilled to give 49.9 g (0.41 mole) of recovered 4-chlorotetrahydropyran (10.2% conversion). The distillation residue was stirred with water for four days at room temperature. The aqueous phase was separated and the water was removed under vacuum. The resulting residue was treated with 0.1 g polyphosphoric acid and distilled at 0.1 mm Hg. The fraction distilling up to 60°C weighed 0.73 g and was shown to be 5,6-dihydro-1,2-pyrone by infrared, nuclear magnetic resonance and mass spectral analyses. The 0.73 g fraction was shown to be 90+% pure 5,6-dihydro-1,2-pyrone by glc analysis.

The water insoluble fraction from the four-day water extraction above was distilled at 0.1 mm Hg to give 1.29 g of distillate which was shown to be 50% 5,6-dihydro-1,2-pyrone by glc analysis. The total yield of 5,6-dihydro-1,2-pyrone amounted to approximately 1.30 g which represents a 28% yield.

Reasonable variation and modification are possible within the scope of the foregoing disclosure and the appended claims to the invention the essence of which is that a halotetrahydropyran is converted by oxidation and dehydrohalogenation, as described and under conditions and with oxygenating or oxidizing gas and a free radical initiator also as described to produce, unexpectedly, a dihydropyrone.

We claim:

1. A process for preparing a 5,6-dihydro-1,2-pyrone comprising the steps of reacting a monohalotetrahydropyran selected from the group consisting of 4-chlorotetrahydropyran, 3-chlorotetrahydropyran, 4-bromotetrahydropyran, 3-bromotetrahydropyran, 4-iodotetrahydropyran, and 3-iodotetrahydropyran with oxygen at a partial $O_2$ pressure of from about 2 to about 200 psig and a temperature of from about 30° to about 180°C in the presence of a free radical initiator selected from the group consisting of 2,2'-azobis(2-methylpropionitrile) (AIBN), di-tert-butyl peroxide, tert-butyl hydroperoxide, cumyl peroxide, benzoyl peroxide, and cumene hydroperoxide, capable of functioning as oxidation initiators under the reaction conditions employed.

2. A process according to claim 1 wherein the halotetrahydropyran is 4-chlorotetrahydropyran.

3. A process for preparing 5,6-dihydro-1,2-pyrone comprising the step of reacting 4-chlorotetrahydropyran with oxygen at a temperature of about 30° to about 180°C, at a partial $O_2$ pressure of from about 2 to about 200 psig, in the presence of 2,2'-azobis(2-methylpropionitrile) for about 0.1 to about 100 hours.

* * * * *